United States Patent
Weiss

(10) Patent No.: US 7,035,004 B2
(45) Date of Patent: Apr. 25, 2006

(54) LASER MICRODISSECTION DEVICE

(75) Inventor: Albrecht Weiss, Linden (DE)

(73) Assignee: Leica Microsystems Wetzlar GmbH, Wetzlar (DE)

( * ) Notice: Subject to any disclaimer, the term of this patent is extended or adjusted under 35 U.S.C. 154(b) by 0 days.

(21) Appl. No.: 10/257,673

(22) PCT Filed: Mar. 29, 2001

(86) PCT No.: PCT/DE01/01227

§ 371 (c)(1),
(2), (4) Date: Nov. 13, 2002

(87) PCT Pub. No.: WO01/78937

PCT Pub. Date: Oct. 25, 2001

(65) Prior Publication Data

US 2003/0133190 A1    Jul. 17, 2003

(30) Foreign Application Priority Data

Apr. 13, 2000 (DE) ............................... 100 18 253

(51) Int. Cl.
*G02B 21/06* (2006.01)

(52) U.S. Cl. ........................ 359/388; 359/381; 359/211; 359/368; 606/17

(58) Field of Classification Search ................ 359/381, 359/388, 368, 557, 209–211, 203; 606/17
See application file for complete search history.

(56) References Cited

U.S. PATENT DOCUMENTS 3,083,611 A * 4/1963 Ziolkowski et al. ........ 250/229
3,626,141 A * 12/1971 Daly ...................... 219/121.68
3,704,949 A * 12/1972 Thomas et al. ................ 356/71
4,061,415 A * 12/1977 Taenzer ...................... 359/210
4,079,230 A * 3/1978 Miyauchi et al. ........ 219/121.8
4,118,109 A * 10/1978 Crawford et al. ........... 359/196
4,407,464 A * 10/1983 Linick ........................ 244/3.13
4,515,447 A * 5/1985 Weimer et al. .............. 359/388

(Continued)

FOREIGN PATENT DOCUMENTS

WO    WO 98/14816 A1    4/1988

*Primary Examiner*—Mark A. Robinson
*Assistant Examiner*—Lee Fineman
(74) *Attorney, Agent, or Firm*—Foley & Lardner LLP

(57) ABSTRACT

The invention relates to a laser microdissection device comprised of a microscope table (1), which supports a specimen (3) to be dissected, of an incident lighting device (7), a laser light source (5) and of an objective (10) for focussing the laser beam (18) of the laser light source (5) onto the specimen (3). According to the invention, the microscope table (1) is not moved during the dissecting process. A laser scanning device (9) is arranged in the incident lighting device (7), is comprised of two thick glass wedge plates (11a, 11b), which are tilted toward the optical axis (8) and can be rotated independently of one another around said optical axis (8). In addition to the beam deviation caused by the wedge angle of the wedge plates (11a, 11b), a beam offset of the laser beam (18) is produced by the thickness and the tilt of the wedge plates (11a, 11b). When both wedge plates (11a, 11b) are rotated, the beam deviation and the beam offset of the laser beam (18) are varied in such a manner that the laser beam (18) always passes through the middle of the objective pupil (19) and, at the same time, the beam is guided over the specimen (3) to be dissected by the beam deviation of the laser beam (18).

8 Claims, 2 Drawing Sheets

U.S. PATENT DOCUMENTS

| | | | |
|---|---|---|---|
| 4,822,974 A | * | 4/1989 | Leighton ............... 219/121.67 |
| 5,045,679 A | * | 9/1991 | Suzuki et al. ............ 250/201.1 |
| 5,202,868 A | * | 4/1993 | Terao et al. ............. 369/44.17 |
| 5,272,325 A | * | 12/1993 | Peng ..................... 235/462.35 |
| 5,486,948 A | * | 1/1996 | Imai et al. .................. 359/462 |
| 5,781,304 A | * | 7/1998 | Kotidis et al. .............. 359/511 |
| 6,052,223 A | * | 4/2000 | Yoneyama et al. ......... 359/381 |
| 6,473,250 B1 | * | 10/2002 | Chapman et al. ........... 359/837 |

* cited by examiner

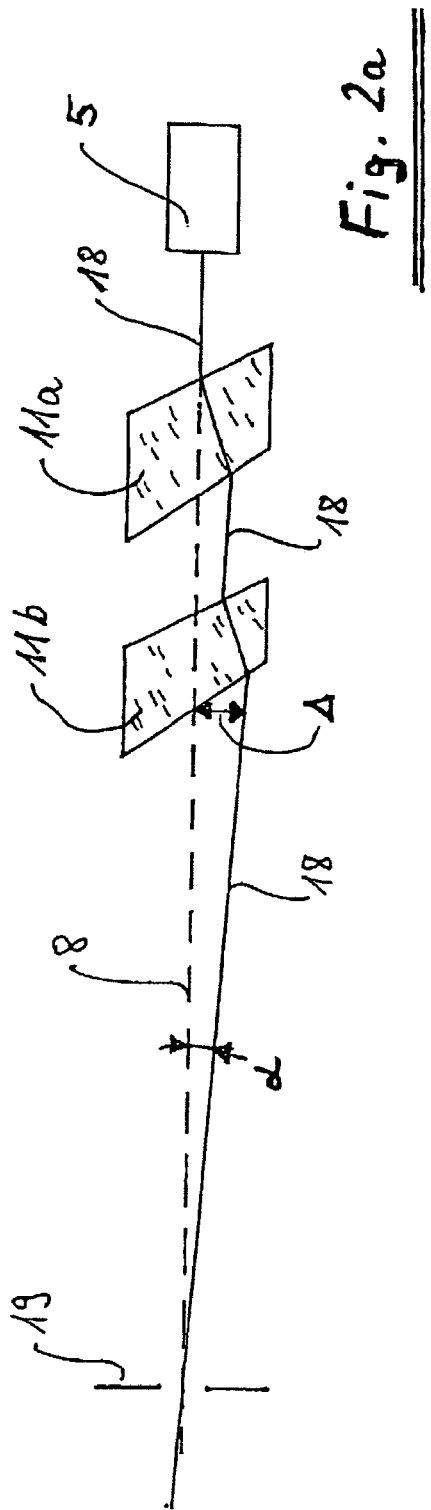
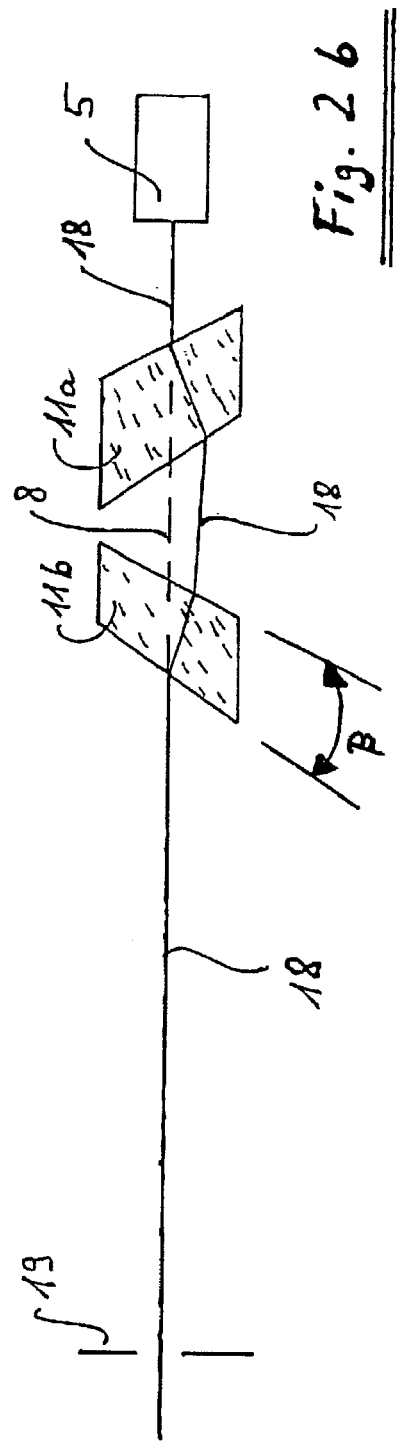

LASER MICRODISSECTION DEVICE

The invention relates to a laser microdissection device having the features of the preamble of independent claim 1.

Known devices for laser microdissection comprise a direct-light instrument, into whose beam path a UV laser beam is introduced. The UV laser light is guided through the direct-light beam path and focused, by a microscope objective, onto a preparation which is placed on a microscope stage (scanning stage) that can be displaced in a motorized fashion. The high energy density produced at the focus by the UV laser light is used for cutting (=dissection) in the preparation. A cutting line is obtained by displacement of the microscope stage during cutting, in order to move the preparation relative to the laser beam, which is static. Operation is generally carried out using pulsed lasers. In this case, a laser pulse produces a small hole in the preparation. A cutting line is obtained by appropriate sequencing of such holes. To that end, in particular in the case of high-magnification objectives, the microscope stage must have a high positioning accuracy in order to make precise cuts possible. Such microscope stages are expensive.

When the preparation is moved around the cutting point of the laser beam, the observer also sees the picture move. This is particularly problematic when observation is being carried out using a slow camera and a monitor. The monitor picture then becomes blurred and exhibits abrupt changes. It would therefore be more favorable for the user if the microscope stage, and therefore the preparation, could remain static during cutting.

If the microscope stage is static, however, then the laser beam needs to be moved over the preparation, which is static. So that the laser beam can be guided over a particular field on the preparation, the laser beam incident in the objective needs to enter the objective pupil at varying angles. This angle variation needs to be carried out by means of a scanning instrument in the x and y directions.

Examples of such scanning instruments are mirror scanners, galvanometer scanners and stepper-motor scanners, as are used in scanning optical microscopes. The scanning instrument in each case needs to be arranged in a plane conjugate with the objective pupil. To that end, so-called pupil imaging is necessary since the deflected beam would not otherwise strike the objective pupil.

The disadvantage of these known scanning instruments is that they require such pupil imaging. In the case of microdissection using UV laser light, UV-compatible pupil imaging would be necessary. In an arrangement with pupil imaging, a series of functional units, for example the aperture-limitation instrument, the offset optics comprising two displaceable lenses, special gray filters etc., need to be arranged between the scanning instrument and the laser. Such a system therefore amounts to a large overall length and takes up a great deal of space. Known scanning instruments, including the drive electronics, are furthermore very expensive.

It is therefore an object of the present invention to provide a compact, simply constructed and inexpensive laser microdissection device, which does not require any pupil imaging and avoids the disadvantages of the prior art.

This object is achieved by a laser microdissection device, having
a microscope stage, which carries a preparation to be cut,
and a direct-light instrument, a laser light source and a microscope objective for focusing the laser light of the laser light source onto the preparation,
which has the following novel features:
a) that the microscope stage is arranged static with respect to the x-y direction during cutting,
b) and that the direct-light instrument contains a laser scanning instrument, which consists of two thick glass wedge plates which are inclined in relation to the optical axis and can be rotated independently of one another about the optical axis, and which produce a beam deflection owing to their wedge angle, the resulting deflection angle $\alpha$ of the laser beam in relation to the optical axis being variable by rotating the glass wedge plates,
c) and that the laser beam has a lateral beam offset in relation to the optical axis at the output of the scanning instrument, owing to the thickness and the oblique setting of the glass wedge plates, and it strikes the middle of the objective pupil of the objective for all deflection angles $\alpha$.

The technical characteristic involves the configuration and spatial arrangement of the two wedge plates.

Optical units which can be used to produce a beam deflection are in fact already known. For instance, it would be conceivable to obtain a beam deflection of the laser beam in the region of the direct-light instrument by passing the laser beam through either an optical unit comprising two mutually displaceable lenses (so-called Abat wedge) or an optical unit comprising two mutually rotatable thin glass wedges. These optical units have the disadvantage, however, that the laser beam experiences only one beam deflection and then arrives outside the pupil of the objective. It therefore no longer reaches the preparation to be cut. Arrangements having said optical units are therefore not suitable for use as a laser scanning instrument.

A laser microdissection device according to the invention therefore has, in the laser beam path, a laser scanning instrument which consists of two thick glass wedge plates. The two glass wedge plates may, for example, have the same wedge angle and different thicknesses as well as different inclinations in relation to the optical axis. Other embodiments of the two wedge plates are conceivable.

Owing to its wedge angle, as is known, each wedge plate produces a component for the overall beam deflection of the laser beam. (The term wedge angle refers to the angle difference between the front external surface and the back external surface of a glass wedge plate.) The two components of the overall beam deflection are added together vectorially. As a result of mutually independent rotation of the two wedge plates about the optical axis, the directions of the two components of the beam deflection are changed. The two components of the beam deflection are added together vectorially to give an overall beam deflection with a deflection angle $\alpha$ of the laser beam in relation to the optical axis. By means of this, the beam deflection produced overall for the laser beam is varied in such a way that the laser beam is guided over the preparation to be cut.

The rotation of the glass wedge plates also causes a change in the beam offset at the output of the scanning instrument. This change in the beam offset compensates for the lateral shift of the laser beam, which is produced in the plane of the objective pupil by the beam deflection. Consequently, the laser beam always passes centrally through the pupil of the objective without variation—irrespective of the deflection angle $\alpha$ that is produced.

Through suitable driving of the rotational movement of the wedge plates, it is possible to produce any deflection angle $\alpha$ and therefore cutting lines of any shape. A parallel setting of the two wedge plates leads to a maximum deflection angle $\alpha$, while an antiparallel arrangement leads to a deflection angle $\alpha=0$ (i.e. the laser beam strikes the preparation along the optical axis). Advantageously, the wedge angles of the two wedge plates are selected to be so large that the laser beam is deviated as far as the edge of the field of view when the deflection angle α is maximum.

With the laser microdissection device according to the invention, it is possible to leave the preparation to be cut in a fixed position and to move the laser cutting point over the preparation with little technical outlay. At the same time, the inventive structure of the laser scanning instrument comprising two thick, inclined, rotatable wedge plates is substantially simpler and less expensive than known beam scanners. In the laser microdissection device according to the invention, an expensive motorized xy stage (scanning stage) may be obviated, since the cutting quality is not dependent on the positioning accuracy of the microscope stage. A laser in the ultraviolet (UV) or infrared (IR) or visible (VIS) spectral range may be used as the laser light source.

When the laser beam deflected by the laser scanning instrument strikes an objective, then for all objective magnifications, as is known, the deviation in the object is proportional to the objective magnification. If the maximum deflection angle α is precisely so large that the laser beam is deflected as far as the edge of the field of view, then this is true for all objectives irrespective of their magnification. This means that the spatial resolution of the laser scanning instrument in the field of view is the same for all objectives. In order to pursue a cutting line over the entire field of view, the same angle settings of the two wedges are successively adopted for all objectives.

This is the great advantage of the laser microdissection device according to the invention, having the described laser scanning instrument, over a previously known laser microdissection device which operates with a static laser beam and an xy stage that is moved. In the case of an xy stage that is moved, its positioning needs to be carried out ever-more accurately as the objective magnification increases, and therefore as the cutting width in the object decreases.

In contrast to this, in the case of the laser scanning instrument according to the invention, a given angle resolution of the wedge rotation for weak objectives with a larger cutting width automatically leads to a larger step size in the object than for strong objectives with a small cutting width.

The fact that the microscope stage is static during the cutting process also has the advantage that the user can observe and control the preparation during the cutting process. For instance, he or she can already select the next desired cutting line at the same time as a cutting process is taking place.

A further advantage of the invention is that no pupil imaging is required and all the functional units, for example the aperture-limitation instrument, the offset optics comprising two displaceable lenses, special gray filters etc., can be integrated in a compact microscope beam path. The device according to the invention therefore has a very compact structure.

In an advantageous embodiment of the laser microdissection device according to the invention, the rotation of the glass wedge plates is carried out in a motorized fashion. To that end, each glass wedge plate is assigned a motor, for example a stepper motor, for rotating the glass wedge plate about the optical axis. The motors receive their control signals from a motor controller. The positioning accuracy of the stepper motors, which are most favorably driven in micro-step operation, then also determines the positioning accuracy of the laser beam on the preparation.

In another advantageous embodiment of the laser microdissection device according to the invention, the rotation of the glass wedge plates is likewise carried out in a motorized fashion. A computer having a mouse and a monitor is additionally provided. The computer is connected to the motor controller and to the laser light source. A camera is furthermore provided which takes a picture of the preparation, said picture being displayed on the monitor. When this embodiment is used, it is possible to produce a laser cut in the preparation by carrying out the following method steps:

a) defining a cutting line on the monitor by means of the mouse, b) computerized division of the cutting line into a series of contiguous cutting holes, the centers of which correspond to the setpoint positions of the laser beam that are to be occupied on the preparation during the cutting process, c) calculating the deflection angle α of the laser beam for each individual position to be occupied, and calculating the associated rotational settings of the glass wedge plates, d) producing the control signals for the motorized rotation of the glass wedge plates, e) and producing the defined cutting line by deflecting the laser beam into the calculated setpoint positions by rotating the glass wedge plates.

Since the described laser scanning instrument permits very exact guidance of the deflected laser beam, other uses of the laser microdissection device according to the invention are also possible. For example, the laser beam deflected by the laser scanning instrument may be used for processing of materials.

In another form of use, the deflected laser beam is guided under computer control, and it is used for scribing surfaces.

In a third form of use of the laser microdissection device according to the invention, the deflected laser beam is used as optical tweezers, by using it to pick up and transfer individual particles.

The invention will be explained in more detail with reference to an exemplary embodiment with the aid of the schematic drawing, in which:

FIG. 2a shows the beam profile of the laser beam when the glass wedge plates are set parallel;

FIG. 2b shows the beam profile of the laser beam when the glass wedge plates are set antiparallel.

In the various figures, equivalent components are denoted by the same reference numerals.

Figure 1:
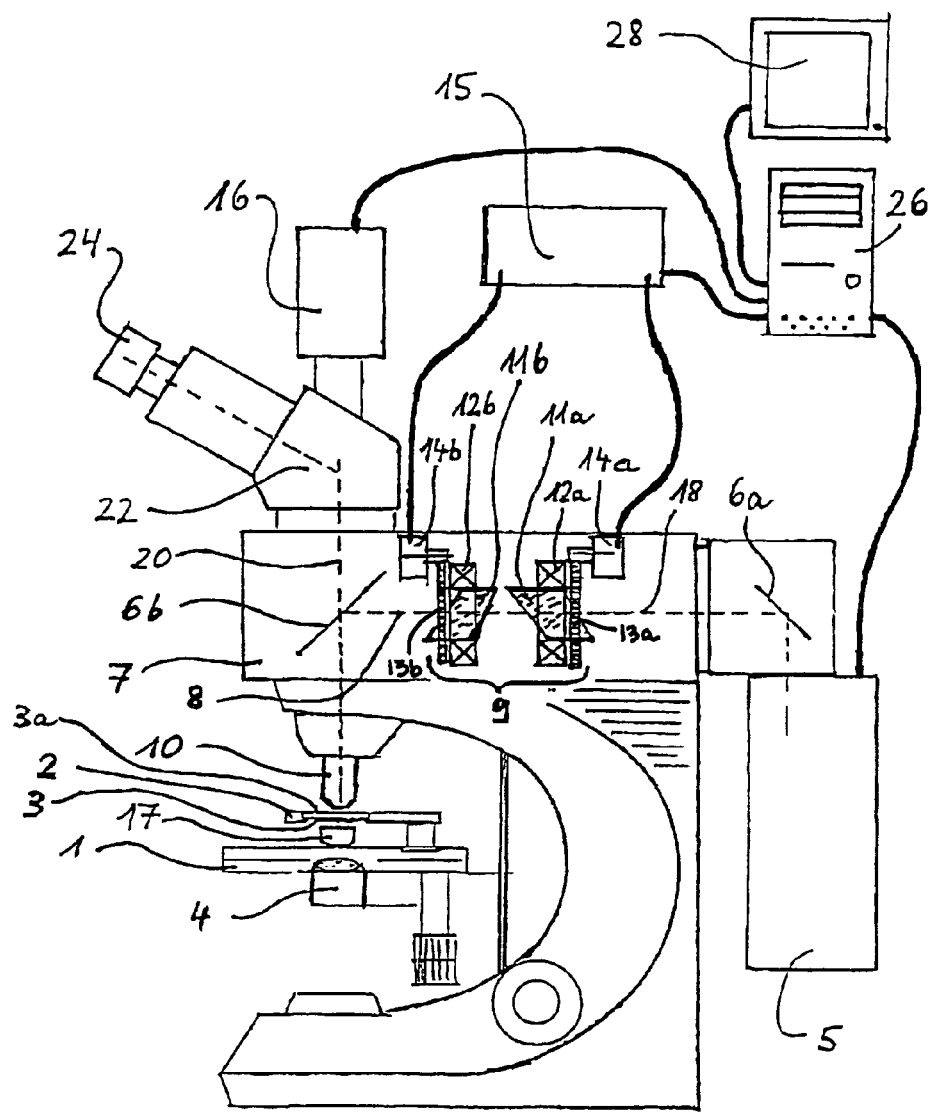
FIG. 1 shows a laser microdissection device according to the invention.

FIG. 1 shows a laser microdissection device according to the invention. The laser microdissection device has a microscope stage 1, on which a preparation holder 2 that carries an object support 3a is arranged, a preparation 3 to be cut being located on the lower side of said object support 3a. A condenser 4, through which the preparation 3 is illuminated, is arranged under the microscope stage 1. During the cutting process, which will be described below, the microscope stage 1 is not displaced horizontally, that is to say in the x direction and in the y direction.

A laser beam is emitted by a laser light source 5, which is here configured as a UV laser light source, and it is introduced via a first deflecting mirror 6a into a direct-light instrument 7 having an optical axis 8. A laser scanning instrument 9 is arranged in the direct-light instrument 7. The laser beam passes through the laser scanning instrument 9 and, via a second deflecting mirror 6b, it reaches an objective 10 which focuses the laser beam onto the preparation 3.

The deflecting mirror 6b is advantageously configured as a dichromatic splitter through which an imaging beam path 20, emerging from the preparation 3 through the objective 10, reaches a tube 22 and eyepieces 24.

The laser scanning instrument 9 consists of two thick glass wedge plates 11a, 11b, which are inclined in relation to the optical axis 8 and can be rotated independently of one another about the optical axis 8. To that end, the wedge plates 11a, 11b are mounted using ball bearings 12. The wedge plate 11a is firmly connected to a toothed wheel 13a, and the wedge plate 11b is firmly connected to a toothed wheel 13b. The wedge plates 11a, 11b are rotated by means of two assigned stepper motors 14a, 14b, the stepper motor 14a engaging with the toothed wheel 13a and the stepper motor 14b engaging with the toothed wheel 13b.

The two stepper motors 14a, 14b are connected to a stepper-motor control unit 15, which delivers the control signals for driving the two stepper motors 14a, 14b. The stepper-motor controller is connected to a computer 26, which has a monitor 28 attached to it. The picture of the preparation 3, taken by a camera 16, is displayed on the monitor 28. A cutting line can be defined on the monitor 28 by means of a computer mouse (not shown). The computer 26 is furthermore connected to the laser light source 5 and supplies the latter with trigger signals for initiating laser pulses when the glass wedge plates 11a, b have been brought into the setpoint position for the cutting line by the stepper motors 14a, b.

When the two glass wedge plates 11a, 11b are rotated, the laser beam appears at the output of the laser scanning instrument 9 with various deflection angles and passes through the objective 10, in each case through the middle of the objective pupil. The laser beam can in this case be guided, by varying the deflection angle, to any positions on the preparation 3 which lie within the field of view of the objective 10. By suitably driving the rotation of the two glass wedge plates 11a, 11b, a cutting line can be produced on the preparation 3. The part of the preparation 3 which is cut out falls through the frame-shaped opening in the preparation holder 2 into a collection vessel 17, which is arranged below the preparation 3 on the microscope stage 1.

The beam profile of the laser beam in the laser scanning instrument 9 is illustrated in FIGS. 2a and 2b. The schematic arrangement of two glass wedge plates 11a, 11b in a laser scanning instrument 9 is shown. In FIG. 2b, for illustration, the wedge angle β of one of the two glass wedge plates (11a, 11b) is represented. The wedge angle β refers to the angle difference between the front external surface and the back external surface of the glass wedge plate (11a, 11b).

A laser beam 18, which is directed at the wedge plates 11a, 11b, is emitted along an optical axis 8 from a laser light source 5. At each glass wedge plate 11a, 11b, owing to the respective wedge angle of the latter, the laser beam 18 experiences a beam deflection. After it has passed through both glass wedge plates 11a, 11b, a deflection angle α is therefore obtained overall.

In addition, owing to the thickness and the inclination of the glass wedge plates 11a, 11b, a beam offset of the laser beam 18 is produced at each of the two glass wedge plates 11a, 11b. Consequently, after it has passed through both glass wedge plates 11a, 11b, the laser beam 18 has, overall, a beam offset Δ which is so large that the laser beam 18 always passes through the middle of an objective pupil 19 of an objective 10 (not shown in detail).

FIG. 2a shows the two glass wedge plates 11a, 11b in a parallel setting. In this case, the largest deflection angle α and the largest beam offset Δ are produced. FIG. 2b shows the two glass wedge plates 11a, 11b in an antiparallel setting. No beam deflection, i.e. a deflection angle α=0, and no beam offset, i.e. Δ=0, are produced in this case.

For all deflection angles α, the beam offset Δ is precisely so large that it exactly compensates for the lateral shift of the deflected beam in the pupil plane, so that the laser beam strikes the middle of the objective pupil 19 for all deflection angles Δ.

By rotating the two wedge plates 11a, 11b about the optical axis 8, the beam deflection and the beam offset of the laser beam 18 are varied in such a way that, for all deflection angles α that are set, the laser beam 18 always passes centrally through the objective pupil 19, so that the laser beam 18 is guided over the preparation 3 to be cut.

The present invention has been described with reference to exemplary embodiments, but it is obvious to any skilled person active in this technical field that modifications and amendments may be made without thereby departing from the scope of protection of the following claims.

LIST OF REFERENCES

| | List of references |
|---|---|
| 1 | microscope stage |
| 2 | preparation holder |
| 3 | preparation |
| 3a | object support |
| 4 | condenser |
| 5 | laser light source |
| 6 | deflecting mirrors a, b |
| 7 | direct-light instrument |
| 8 | optical axis |
| 9 | laser scanning instrument |
| 10 | objective |
| 11 | glass wedge plates (11a, 11b) |
| 12 | ball bearing |
| 13 | toothed wheels (13a, 13)b |
| 14 | stepper motors (14a, 14b) |
| 15 | motor controller |
| 16 | camera |
| 17 | collection vessel |
| 18 | laser beam |
| 19 | objective pupil |
| 20 | imaging beam path |
| 22 | tube |
| 24 | eyepiece |
| 26 | computer |
| 28 | monitor |
| α | deflection angle |
| β | wedge angle |
| Δ | beam offset |

The invention claimed is:

1. A laser microdissection device, having
a microscope stage, which carries a preparation to be cut,
a direct-light instrument having an optical axis,
a laser light source for producing a laser beam,
and a microscope objective for focusing the laser beam onto the preparation, wherein
a) the microscope stage is arranged static with respect to the x direction and the y direction during cutting,
b) the direct-light instrument contains a laser scanning instrument, which consists two thick glass wedge plates which are inclined in relation to the optical axis and can be rotated independently of one another about the optical axis, and which produce a beam deflection owing to their wedge angle, the resulting deflection angle α of the laser beam in relation to the optical axis being variable by rotating the glass wedge plates, c) and only the glass wedge plates causing the laser beam to have a lateral beam offset in relation to the optical axis at the output of the laser scanning instrument, owing to the thickness and the oblique setting of the glass wedge plates, and only the glass wedge plates causing the laser beam to always strike the middle of an objective pupil of the objective for all deflection angles α.

2. The laser microdissection device as claimed in claim 1, wherein
the laser light source is a UV laser or an IR laser or a VIS laser.

3. The laser microdissection device as claimed in claim 1, wherein
a) each glass wedge plate is assigned a motor for rotating the glass wedge plate about the optical axis, and
b) the motors are assigned a motor controller.

4. The laser microdissection device as claimed in claim 1, wherein
a) each glass wedge plate is assigned a motor for rotating the glass wedge plates about the optical axis,
b) the motors are assigned a motor controller,
c) a computer having a mouse and a monitor is provided, the computer being connected to the motor controller and to the laser light source,
d) a camera is provided which takes a picture of the preparation, said picture being displayed on the monitor.

5. A method using the laser microdissection device as claimed in claim 4, comprising:

a) defining a cutting line on the monitor by means of the mouse,
b) computerized dividing of the cutting line into a series of contiguous cutting holes, the centers of which correspond to the setpoint positions of the laser beam that are to be occupied on the preparation during the cutting process,
c) calculating the deflection angle α of the laser beam for each individual position to be occupied, and calculating the associated rotational settings of the glass wedge plates,
d) producing the control signals for the motorized rotation of the glass wedge plates,
e) and producing the defined cutting line by deflecting the laser beam into the calculated setpoint positions by rotating the glass wedge plates.

6. The method of using the laser microdissection device as claimed in claim 5, further comprising:
guiding the deflected laser beam under computer control, and scribing surfaces with the deflected laser beam.

7. A method of using the laser microdissection device as claimed in claim 1, comprising:
processing materials by the laser beam being deflected by the laser scanning instrument.

8. A method of using the laser microdissection device as claimed in claim 1, comprising:
picking up and transferring individual particles with the deflected laser beam, which is used as an optical tweezers.

* * * * *